United States Patent [19]

Molnar et al.

[11] 4,196,206

[45] Apr. 1, 1980

[54] PYRIDYL-PIPERAZINE DERIVATIVE WITH ANTI-ARRYTHMIC EFFECT

[75] Inventors: Arpád Molnár; Károly Felföldi; Mihály Bartók, all of Szeged; Egon Kárpáti; László Szporny, both of Budapest, all of Hungary

[73] Assignee: Richter Gedeon Vegyeszeti Gyar RT, Budapest, Hungary

[21] Appl. No.: 880,364

[22] Filed: Feb. 23, 1978

[30] Foreign Application Priority Data

Feb. 25, 1977 [HU] Hungary ................................ RI 617

[51] Int. Cl.$^2$ .................... A61K 31/495; C07D 401/04
[52] U.S. Cl. ....................................... 424/250; 544/360
[58] Field of Search ......................... 424/250; 544/360

[56] References Cited

U.S. PATENT DOCUMENTS

| | | | |
|---|---|---|---|
| 2,958,694 | 11/1960 | Janssen | 260/268 |
| 4,038,279 | 7/1977 | Renth | 260/268 BP |

OTHER PUBLICATIONS

Chem. Abst. vol. 83, 1975, 164239q.

*Primary Examiner*—Alton D. Rollins
*Assistant Examiner*—Lisa Jones
*Attorney, Agent, or Firm*—Karl F. Ross

[57] ABSTRACT

3-[4-(2'-Pyridyl)-piperazin-1-yl]-1-(3,4,5-trimethoxybenzoyloxy)-propane or a pharmaceutically acceptable acid-addition salt thereof in a composition with anti-arrhythmic activity.

4 Claims, No Drawings

PYRIDYL-PIPERAZINE DERIVATIVE WITH ANTI-ARRYTHMIC EFFECT

The invention relates to novel pyridyl-piperazine derivative having valuable pharmacological properties. More particularly, the subject matter of the invention is the 3-[4-(2'-pyridyl)-piperazin-1-yl]-1-(3,4,5-trimethoxy-benzoyloxy)-propane and acid-addition salts thereof.

In the U.S. Pat. No. 2,958,694 1-(trimethoxybenzoyl-lower alkylene)-4-(2'-pyridyl)-piperazines are described; these aromatic aminoketones exert sedative action on the central nervous system. The novel compound of the present invention is an ester-type compound and acts on the heart function with an anti-arrhythmic activity surpassing that of the hitherto known compounds having similar pharmacological properties.

The extent of anti-arrhythmic activity was measured on narcotized cats in the following way: the threshold value of electric heart fibrillation was measured on groups of six animals each, and then the six animals of one group were treated with 1 mg./kg. i.v. doses of the compound of the invention, while six animals of another group were treated with 1 mg./kg. i.v. doses of quinidine (used as the reference material); the increase of the threshold value of heart fibrillation was then measured and expressed in percentages related to the corresponding values obtained before the treatment with the drugs [cf. L. Szekeres and J. Papp: British J. Pharmacol. 17, 167 (1967)]. While with quinidine, which is a well known anti-arrhythmic drug used successfully in therapy, the increase of the threshold value of fibrillation was only 20.6%, the new compound of the invention caused a much higher increase: 36.4%.

The new 3-[4-(2'-pyridyl)-piperazin-1-yl]-1-(3,4,5-trimethoxy-benzoyloxy)-propane and the acid-addition salts thereof are prepared according to the invention by (a) reacting 3-[4-(2'-pyridyl)-piperazin-1-yl]-1-hydroxy-propane with 3,4,5-trimethoxy-benzoic acid or with a reactive derivative thereof or by (b) reacting 4-(2'-pyridyl)-piperazine with a 1-(3,4,5-trimethoxy-benzoyloxy)-3-halogen-propane, and, if desired, converting the obtained product into an acid-addition salt.

According to an advantageous method of process-variant (a) the starting 3-[4-(2'-pyridyl)-piperazin-1-yl]-1-hydroxy-propane is reacted with 3,4,5-trimethoxybenzoic acid. This reaction is performed suitably in the presence of an activator for the carboxyl group and/or of a dehydrating agent. Halogenated phenols or nitro-halo-phenols, preferably pentachlorophenol and/or N,N'-dicyclohexyl-carbodiimide may be used as the activators or dehydrating agent, respectively.

According to another preferred method of performance, the 3-[4-(2'-pyridyl)-piperazin-1-yl]-1-hydroxy-propane is reacted with a derivative of the 3,4,5-trimethoxy-benzoic acid suited for acylating reactions. Such derivatives may be the acid anhydride, the acid halides or esters of the acid formed with aliphatic alcohols having 1 to 5 carbon atoms.

When 3,4,5-trimethoxy-benzoic acid halides are used as acylating agents, the acid chloride is preferred for this purpose and the molar ratio of the acid halide to the hydroxy compound may be 1:1.0 to 1:1,1. The reaction may be carried out in an inert anhydrous organic solvent, e.g. in a compound of the benzene series, such as benzene, toluene or xylene, or in an aliphatic ketone, such as acetone, methyl-isobutyl ketone or in an aliphatic alcohol having 1 to 5 carbon atoms. The reaction temperatures may vary within wide limits. It is, however, preferred to add the acylating agent under cooling, suitably at a temperature between 0° and 30° C., to the solution of the starting hydroxy-compound and then keep the reaction mixture at elevated temperature, preferably at the boiling temperature thereof. The obtained acid-addition salt of the reaction product can be precipitated directly and separated by filtration.

When using as the acylating agent an ester of 3,4,5-trimethoxy-benzoic acid formed with an aliphatic alcohol having 1 to 5 carbon atoms, the acylation reaction is carried out preferably in the presence of a catalytic amount of an alkali alkoxide, such as sodium or potassium methoxide or ethoxide. The acylating agent is used in a slight excess.

The reaction is performed in the presence of one of the solvents mentioned above, or in the absence of solvents.

The reaction temperature may vary within wide limits, in general between 35° C. and 150° C. Preferably, the reaction is carried out at the boiling temperature of the reaction mixture; in this case the lower aliphatic alcohol formed in the reaction can be removed by distillation. The resulting product can be separated from the reaction mixture after dissolving the crude reaction product in one of the solvents mentioned above, e.g. by an extraction.

The variant (b) of the process of the invention is performed by reacting 4-(2'-pyridyl)-piperazine with a 1-(3,4,5-trimethoxy-benzoyloxy)-3-halogen-propane. As the 3-halogen-derivative, preferably the corresponding 3-chloro-or 3-bromo-derivatives may be used.

This reaction is carried out in the presence of an aliphatic ketone or alcohol having 1 to 5 carbon atoms or of a hydrocarbon of the benzene series such as benzene, toluene or xylene, at elevated temperature, preferably at the boiling temperature of the reaction mixture; the resulting product is recovered e.g. by an extraction.

The product obtained by the process of the invention may be isolated and purified by known methods, but it may be also converted into an acid-addition salt without previous purification.

The acid-addition salts can be prepared with inorganic or organic acids, such as hydrohalides, e.g. hydrogen chloride, bromide or iodide, sulfuric acid, phosphoric acids, acetic, propionic, butyric, maleic, fumaric, citric, malic, and tartaric acids.

In human therapy, the new compound of the invention is administered preferably orally or intravenously. The daily dose may be about 1 to 10 mg., preferably 3 to 7 mg./kg. body weight; a single oral or intravenous dosis may be, depending on the seriousness of the disease, between 1.0 and 3.0 mg./kg. body weight.

The compounds of the invention can be formed into pharmaceutical compositions by admixing with the commonly usual inert, non-toxic solid or liquid pharmaceutical carriers and/or excipients. Suitable carriers and excipients include e.g. water, gelatine, lactose, starch, talc, magnesium stearate, vaseline, acacia, vegetable oils, polyethylene glycols and the like. The compositions can contain also various auxiliary materials, e.g. preserving, stabilizing, wetting or emulsifying agents, buffers or flavoring additives.

The preparation of the compounds of the invention is illustrated in greater detail by the following Examples.

EXAMPLE 1

3-[4-(2'-Pyridyl)-piperazin-1-yl]-1-(3,4,5-trimethoxybenzoyloxy)-propane dihydrochloride (a) 25 g. (0.153 moles) of 4-(2'-pyridyl)-piperazine, 15.5 g. (0.164 moles) of 3-chloro-1-hydroxy-propane and 23 g. of anhydrous potassium carbonate are added to 120 ml. of ethanol and the mixture is heated under reflux for 20 hours, and then cooled to room temperature. The precipitated inorganic salt is filtered off, the filtrate is evaporated and the evaporation residue dissolved in 80 ml. of 20% aqueous hydrochloric acid. The acid solution is washed with 30 ml. of benzene; the separated acidic aqueous phase is adjusted to pH=9 with 30% aqueous sodium hydroxide solution. The thus alkalinized solution is extracted with 100 ml. of benzene, the benzene phase is dried over anhydrous sodium sulfate, filtered and evaporated to dryness. The evaporation residue is dissolved in diethyl ether, and product is crystallized by cooling. The obtained crystals are collected by filtration and dried. 27 g. of 3-[4-(2'-pyridyl)-piperazin-1-yl]-1-hydroxy-propane (80% of the theoretical yield) are obtained; m.p. 80° to 81° C.

| Elemental analysis for $C_{12}H_{19}N_3O$: | | | |
| --- | --- | --- | --- |
| calculated: | C 65.20; | H 8.68; | N 18.55% |
| found: | C 65.32; | H 8.74; | N 18.30%. |

(b) 2.2 g. (0.1 mole) of the product of Example 1(a) are dissolved in 15 ml. of ethanol and the resulting solution is added dropwise to the solution of 2.4 g. (0.0105 moles) of 3,4,5-trimethoxy-benzoyl chloride in 20 ml. of acetone. The mixture is heated under reflux for 15 minutes and after cooling is saturated with hydrogen chloride gas. The solution with the crystals formed therein is allowed to stand at between 0° and 5° C., and then the obtained crystals are separated by filtration and dried. The obtained crude product may be purified, if necessary, by recrystallization from a mixture of water and ethanol.

3.5 g. of 3-[4-(2'-pyridyl)-piperazin-1-yl]-(3,4,5-trimethoxy-benzoyloxy)-propane dihydrochloride (72% of the theoretical yield are obtained; m.p.: 200°–201° C.

| Elemental analysis for $C_{22}H_{31}Cl_2N_3O_5$: | | | |
| --- | --- | --- | --- |
| calculated: | C 54.10; | H 6.40; | N 14.52%; |
| found: | C 54.05; | H 6.32; | N 14.62%. |

EXAMPLE 2

0.3 g. of sodium metal is dissolved in 10 ml. of anhydrous ethanol and then 5.5 g. (0.024 moles) of 3-[4-(2'-pyridyl)-piperazin-1-yl]-1-hydroxy-propane (prepared according to paragraph (a) of Example 1) and 6.2 g. (0.028 moles) of 3,4,5-trimethoxy-benzoic acid methyl ester are added to the solution. The reaction mixture is heated at 140° C. for three hours, during which time the methanol formed in the reaction is distilled off. The resulting reaction mixture is dissolved in 30 ml. of 20% hydrochloric acid solution, the acid solution is extracted with 30 ml. of benzene and the phases are allowed to separate. The separated aqeuous phase is made alkaline to pH=8 by the addition of 30% aqueous sodium hydroxide solution, and the alkaline solution is extracted with 100 ml. of benzene. The separated benzene solution is dried over anhydrous sodium sulfate, filtered and the filtrate is saturated with hydrogen chloride gas under cooling. The precipitated acid addition salt is collected by filtration, dried and recrystallized, if necessary, from a mixture of water and ethanol.

7 g. of 3-[4-(2'-pyridyl)-piperazine-1-yl]-1-(3,4,5-trimethoxy-benzoyloxy)-propane dihydrochloride (59% of the theoretical yield) are obtained.

EXAMPLE 3

3.3 g. (0.02 moles) of 4-(2'-pyridyl)-piperazine, 6.4 g. (0.022 moles) of 1-(3,4,5-trimethoxy-benzoyloxy)-3-chloro-propane and 3.1 g. of anhydrous potassium carbonate are added to 30 ml. of xylene. The mixture is heated under reflux while stirring for 20 hours and then cooled to room temperature. 30 ml. of benzene are added to the cooled reaction mixture, which is then washed with water. The phases are separated, the benzene solution is dried over anhydrous sodium sulfate, filtered and the filtrate is saturated with hydrochloric acid gas under cooling. The precipitated acid addition salt is collected by filtration, dried and recrystallized from a mixture of ethanol and water.

5.0 g. of 3-[4-(2'-pyridyl)-piperazin-1-yl]-1-(3,4,5-trimethoxy-benzoyloxy)-propane dihydrochloride (51% of the theoretical yield) are obtained.

EXAMPLE 4

Preparation of tablets containing 3-[4-(2'-pyridyl)-piperazin-1-yl]-1-(3,4,5-trimethoxy-benzoyloxy)-propane dihydrochloride as an active substance The following ingredients are used for the preparation of 1000 tablets:

| 3-[4-(2'-pyridyl)-piperazin-1-yl]-1-(3,4,5-trimethoxy-benzoyloxy)-propane dihydrochloride | 30 g. |
| --- | --- |
| talc | 9 g. |
| magnesium stearate | 3 g. |
| polyvinyl-pyrrolidone | 6 g. |
| potato starch | 84 g. |
| lactose | 168 g. |

The active substance is admixed with the lactose and with a part of the potato starch, the dry mixture is then wetted with an aqueous solution of the polyvinylpyrrolidone. The wet mixture is granulated in the usual way, the dry granules are admixed with the talc, the magnesium stearate and the residual part of the potato starch. The mixture is then pressed in the usual way to form 1000 tablets each containing 30 mg. of the active substance.

What we claim is:

1. A pharmaceutical composition, which comprises as the active ingredient, 3-[4-(2'-pyridyl)-piperazin-1-yl]-1-(3,4,5-trimethoxy-benzoyloxy)-propane or a pharmaceutically acceptable acid-addition salt thereof, in admixture with a pharmaceutically acceptable diluent.

2. The composition defined in claim 1 wherein the active ingredient is 3-[4-(2'-pyridyl)-piperazin-1-yl]-1-(3,4,5-trimethoxy-benzoyloxy)-propane dihydrochloride.

3. A method of treatment of heart dysfunction in an animal subject which comprises administering to the subject an antiarrythmically effective amount of 3-[4-(2'-pyridyl)-piperazin-1-yl]-1-(3,4,5-trimethoxy-benzoyloxy)-propane or a pharmaceutically acceptable acid-addition salt thereof.

4. The method defined in claim 3 wherein 3-[4-(2'-pyridyl)-piperazin-1-yl]-1-(3,4,5-trimethoxy-benzoyloxy)-propane dihydrochloride is administered.

* * * * *